(12) United States Patent
Krishnan

(10) Patent No.: US 7,492,933 B2
(45) Date of Patent: Feb. 17, 2009

(54) COMPUTER-AIDED DETECTION SYSTEMS AND METHODS FOR ENSURING MANUAL REVIEW OF COMPUTER MARKS IN MEDICAL IMAGES

(75) Inventor: Arun Krishnan, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 649 days.

(21) Appl. No.: 10/798,593

(22) Filed: Mar. 11, 2004

(65) Prior Publication Data

US 2004/0223633 A1 Nov. 11, 2004

Related U.S. Application Data

(60) Provisional application No. 60/453,564, filed on Mar. 11, 2003.

(51) Int. Cl.
*G06K 9/00* (2006.01)
(52) U.S. Cl. ....................................... 382/128
(58) Field of Classification Search ......... 382/128–132; 128/922; 322/1
See application file for complete search history.

(56) References Cited

U.S. PATENT DOCUMENTS

| | | | | |
|---|---|---|---|---|
| 5,289,374 | A | 2/1994 | Doi et al. | 364/413.13 |
| 5,801,810 | A | 9/1998 | Roenker | 351/246 |
| 6,014,452 | A | 1/2000 | Zhang et al. | 382/132 |
| 6,108,439 | A * | 8/2000 | Ishiguro | 382/131 |
| 6,266,435 | B1 * | 7/2001 | Wang | 382/132 |
| 6,418,237 | B1 * | 7/2002 | Takeo | 382/128 |
| 7,072,501 | B2 * | 7/2006 | Wood et al. | 382/132 |
| 7,162,061 | B1 * | 1/2007 | Takeo | 382/128 |
| 2002/0076091 | A1 * | 6/2002 | Wang | 382/132 |
| 2002/0097902 | A1 * | 7/2002 | Roehrig et al. | 382/132 |

FOREIGN PATENT DOCUMENTS

| | | |
|---|---|---|
| JP | 2000276587 A | 10/2000 |
| JP | 2002112986 A | 4/2002 |
| WO | WO 02056240 A1 | 7/2002 |

OTHER PUBLICATIONS

Suzuki et al., "Neural filter with selection of input features and its application to image quality improvement of medical image sequences", IEEE International Symposium on Intelligent Signal Processing and Communication Systems, Nov. 5, 2000, pp. 783-788.
Manning, D.J, "Evaluation of diagnostic performance in radiography", Radiography (1998), pp. 49-60, The College of Radiographers.

* cited by examiner

*Primary Examiner*—Jingge Wu
*Assistant Examiner*—Andrae S Allison

(57) ABSTRACT

CAD (computer-aided detection) systems, methods and tools are provided for automatically inserting "false" marks (e.g., incorrect marks, misleading marks, etc.) in medical images to ensure an unbiased CAD-assisted review of the marked medical images by physicians, clinicians, radiologists, etc. For example, a method for automatic detection of medical conditions in medical images includes the steps of receiving image data, processing the image data to detect potential medical conditions in the image data, adding a mark in the image data that indicates a detected medical condition, adding a false mark in the image data; and outputting marked image data comprising one or more marks that indicate a detected medical condition, or one or more false marks, or both. The individual performing a CAD-assisted review of the "marked" image data is aware that one or more "false" marks may be included in displayed images, which prevents blind reliance on the CAD results.

20 Claims, 3 Drawing Sheets

COMPUTER-AIDED DETECTION SYSTEMS AND METHODS FOR ENSURING MANUAL REVIEW OF COMPUTER MARKS IN MEDICAL IMAGES

CROSS-REFERENCE TO RELATED APPLICATION

This application claims priority to U.S. Provisional application Ser. No. 60/453,564, filed on Mar. 11, 2003, which is fully incorporated herein by reference.

TECHNICAL FIELD OF THE INVENTION

The present invention relates generally to CAD (Computer Aided Detection) systems, methods and tools for automatic detection and marking of features of interest in medical images and, in particular, to CAD systems, methods and tools that automatically insert "false" marks (e.g., incorrect marks, misleading marks, etc.) in medical images to ensure an unbiased CAD-assisted review of the marked medical images by physicians, clinicians, radiologists, etc.

BACKGROUND

In the field of medical imaging, various systems have been developed for generating medical images of various anatomical structures of individuals for the purpose of screening and evaluating medical conditions. These imaging systems include, for example, CT (computed tomography) imaging, MRI (magnetic resonance imaging), X-ray systems, ultrasound systems, PET (positron emission tomography) systems, etc. Each imaging modality may provide unique advantages over other modalities for screening and evaluating certain types of diseases, medical conditions or anatomical abnormalities, including, for example, colonic polyps, aneurisms, lung nodules, calcification on heart or artery tissue, cancer microcalcifications or masses in breast tissue, and various other lesions or abnormalities.

For example, as is well-known in the art, CT (computed tomography) imaging systems can be used to obtain a set of cross-sectional images or 2D "slices" of a ROI (region-of-interest) of a patient for purposes of imaging organs and other anatomies. The CT imaging modality is commonly employed for purposes of diagnosing disease because such modality provides precise images that illustrate the size, shape, and location of various anatomical structures such as organs, soft tissues, and bones, and also enables a more accurate evaluation of lesions and abnormal anatomical structures such as cancer, polyps, etc.

One conventional method that physicians, clinicians, radiologists, etc., use for diagnosing and evaluating medical conditions is to manually review hard-copies (X-ray films, prints, photographs, etc) of medical images that are reconstructed from an acquired image dataset, to discern characteristic features of interest. For example, CT image data that is acquired during a CT examination can be used to produce a set of 2D medical images (X-ray films) that can be viewed to identify potential abnormal anatomical structures or lesions, for example, based upon the skill and knowledge of the reviewing physician, clinician, radiologist, etc. For example, a mammogram procedure may produce medical images that include normal anatomical structures corresponding to breast tissue, but a trained radiologist may be able identify small lesions among these structures that are potentially cancerous. However, a trained radiologist, physician or clinician may misdiagnose a medical condition such as breast cancer due to human error.

Accordingly, various image data processing systems and tools have been developed to assist physicians, clinicians, radiologists, etc, in evaluating medical images to diagnose medical conditions. For example, CAD (computer-aided detection) tools have been developed for various clinical applications to provide automated detection of medical conditions in medical images. In general, CAD systems employ methods for digital signal processing of image data (e.g., CT data) to automatically detect lesions and other abnormal anatomical structures such as colonic polyps, aneurisms, lung nodules, calcification on heart or artery tissue, micro calcifications or masses in breast tissue, etc.

More specifically, conventional CAD tools include methods for analyzing image data to automatically detect and mark regions of features of interest in the image data which are identified as being potential lesions, abnormalities, disease states, etc. When the marked image data is rendered and displayed, the marked regions or features are "marked" or otherwise highlighted to direct the attention of the radiologist to potential medical conditions in medical image.

Although CAD systems can be very useful for diagnostic purposes, various governmental agencies (such as the FDA) and other groups are concerned that physicians may become too dependent on CAD systems and blindly rely on the CAD findings without conducting an independent review/analysis of the medical images to confirm/verify/reject potential medical conditions as indicated by the computer-generated marks. Indeed, if a physician becomes too reliant and trusting of a CAD tool that he/she uses on a regular basis, the physician may misdiagnose a potential medical condition, or otherwise fail to identify a potential medical condition, if the CAD process generates incorrect results. For instance, the results of a CAD analysis can include "false positives" by incorrectly marking normal regions, or the CAD analysis may result in "unmarked" but nonetheless abnormal regions.

In such instances, the physician's blind reliance on incorrect CAD marks could result in significant/substantial changes in a patient management process due to extra testing or biopsies, time lost by the radiologist, increased healthcare costs, trauma to the patient, and lead to a lack of trust in computer-assisted diagnosis systems.

SUMMARY OF THE INVENTION

Exemplary embodiments of the invention generally include CAD (computer aided detection) systems, methods and tools for automatic detection and marking of features of interest in medical images. More specifically, exemplary embodiments of the invention include CAD systems, methods and tools that automatically insert "false" marks (e.g., incorrect marks, misleading marks, etc.) in medical images to ensure an unbiased CAD-assisted review of the marked medical images by physicians, clinicians, radiologists, etc.

In accordance with CAD systems, tools and methods according to exemplary embodiments of the invention, it is assumed that the individual performing a CAD-assisted review of "marked" images generated by a CAD tool is aware that one or more "false" marks (or annotations) may be included in displayed images, which are incorrect or purposefully misleading, for example. A CAD process according to the invention is designed to ensure that a physician does not have complete trust in the computer-generated CAD marks of a displayed image, thus compelling the reviewer to carefully review each marked and unmarked region in the display image, rather than relying blindly on the CAD results.

In one exemplary embodiment of the invention, a CAD system, tool or method can add either a fixed or random number of false marks to an image dataset, wherein false marks may be randomly inserted in regions that are determined to not have abnormal structures or lesions, or wherein false marks may be inserted to mark anatomical structures that resemble lesions or anomalies of interest. For instance, when diagnosing for cancer, false marks may be added to regions that include scar tissue, which may have features similar to cancer.

In another exemplary embodiment of the invention, rather than always adding a fixed number of false marks, a CAD system, tool or method can add a random number of marks for each invocation of a detection process. For instance, a random number of false marks may include the addition of zero (0) marks or 1 or more false marks.

In yet another exemplary embodiment of the invention, a CAD system, tool or method may randomly perturb the location of a computer-generated mark, to ensure that a physician analyzes regions/locations surrounding and including the computer-generated marks. For example, a CAD process may shift a mark from a location where a potential lesion or abnormality is believed to be located, thus ensuring that the physician carefully reviews the area surrounding the mark.

In another exemplary embodiment of the invention, a CAD system, tool or method can generate marked images having possible false marks, but also unmarked regions or locations in a medical image that are determined to actually have potential lesions or abnormalities, but the marks are purposefully excluded. In this manner, if the physician is aware that a marked image output from the CAD process may not include all marks for regions or features detected by the CAD detection system, the physician will be compelled to carefully review the marked image.

These and other exemplary embodiments, features and advantages of the present invention will be described or become apparent from the following detailed description of exemplary embodiments, which is to be read in connection with the accompanying drawings.

DETAILED DESCRIPTION OF EXEMPLARY EMBODIMENTS

Exemplary embodiments of the invention described herein generally include CAD (computer aided detection) systems, methods and tools for automatic detection and marking of features of interest in medical images. More specifically, exemplary embodiments of the invention include CAD systems, methods and tools that automatically insert "false" marks (e.g., incorrect marks, misleading marks, etc.) in medical images to ensure an unbiased CAD-assisted review of the marked medical images by physicians, clinicians, radiologists, etc.

Figure 1:
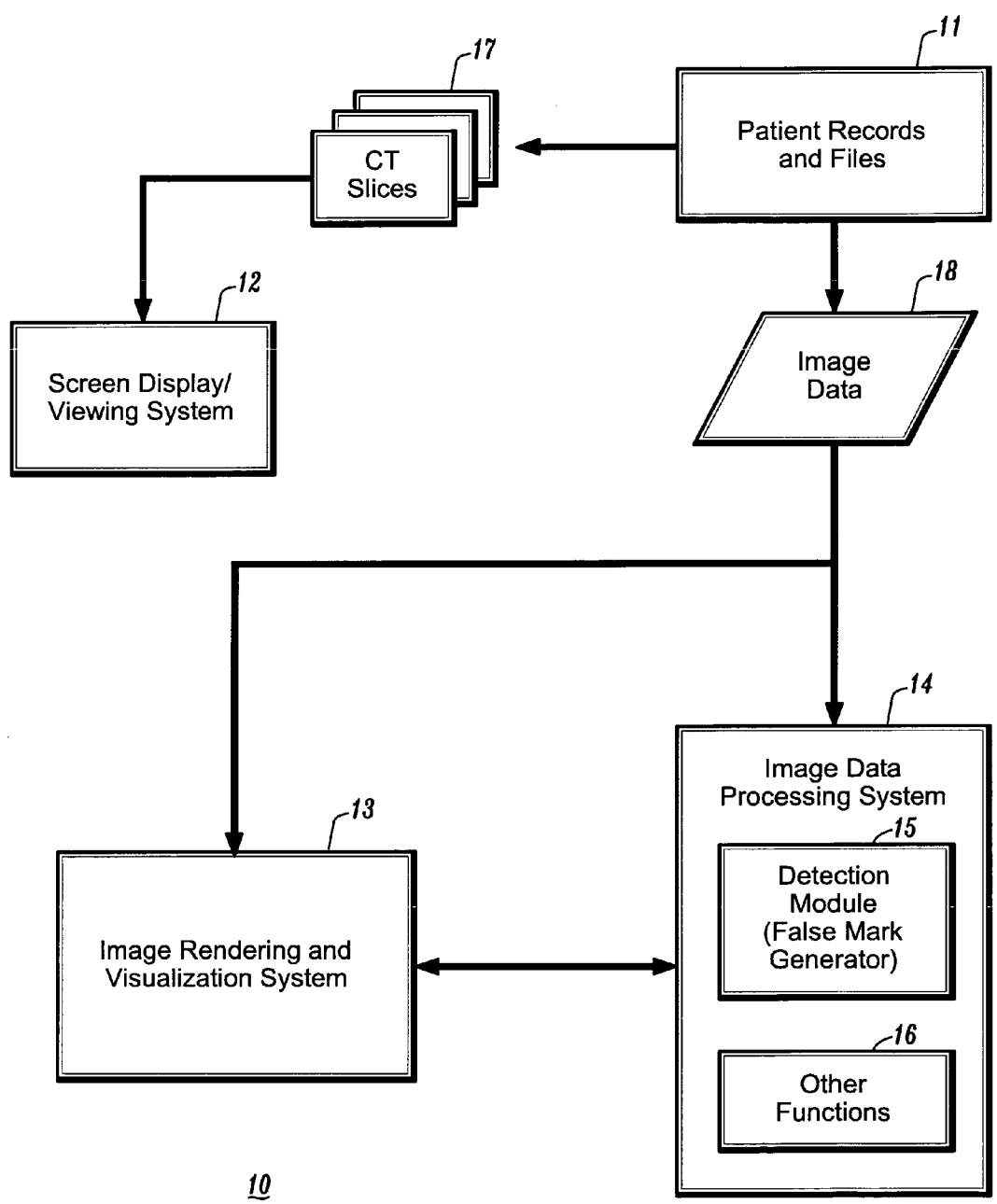
FIG. 1 is a schematic diagram of a system for analyzing patient image data according to an exemplary embodiment of the invention which comprises a CAD tool that adds false or misleading marks in medical images to ensure physician review and analysis of patient image data.
Figure 2:
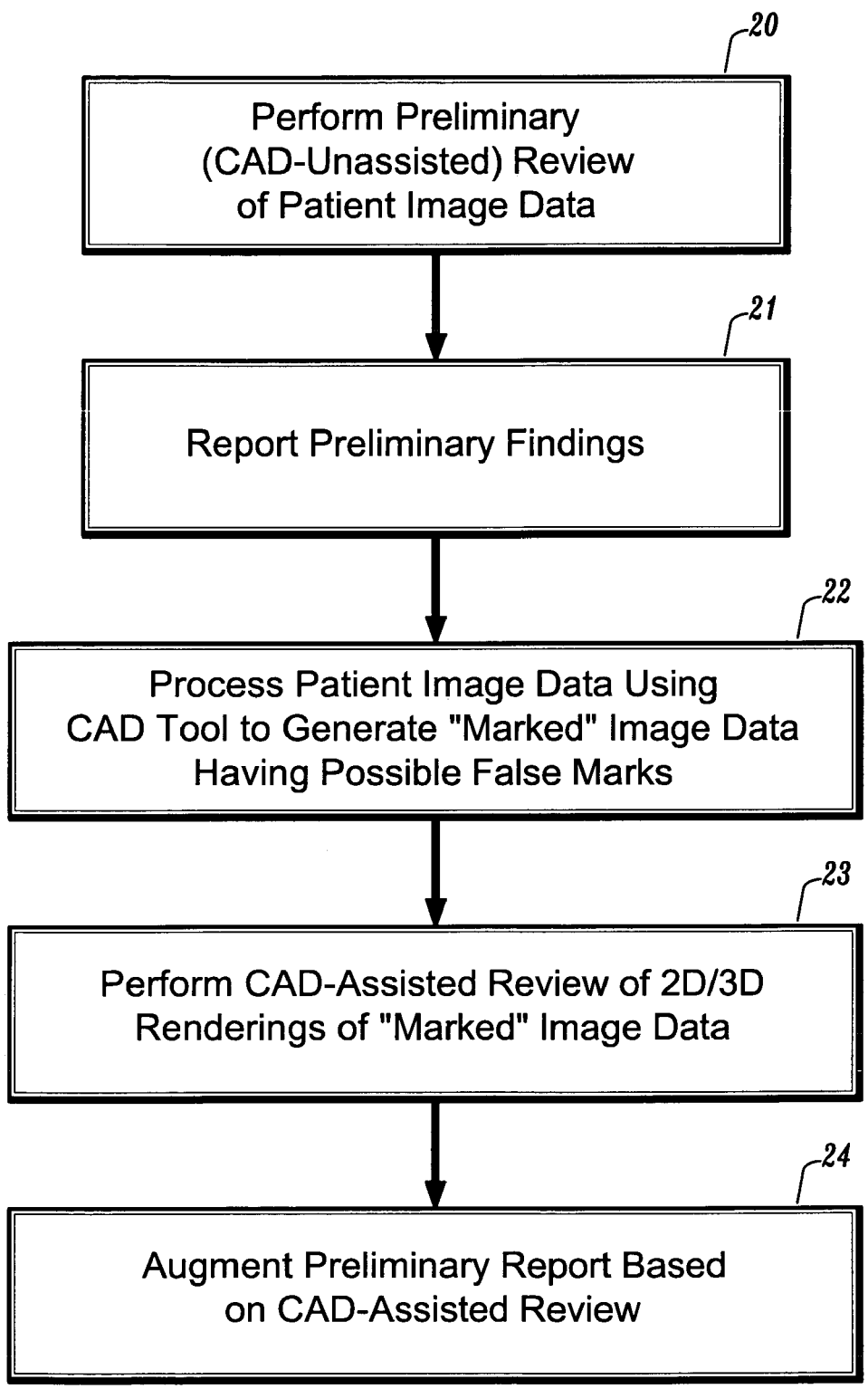
FIG. 2 is a flow diagram of a workflow process for physician review of patient data using the system of FIG. 1, according to an exemplary embodiment of the invention.

Exemplary embodiments of the invention will be described herein with reference to FIGS. 1, 2 and 3. In general, FIG. 1 is a diagram that illustrates a system for analyzing medical images according to an exemplary embodiment of the invention. As explained below, the exemplary system of FIG. 1 comprises a CAD system/tool that includes one or more methods according to exemplary embodiments of the invention (which are discussed in detail with reference to FIG. 3, for example) for automatically detecting and correctly marking potential abnormal anatomical structures in an subject image dataset, and for falsely marking one or more regions in the image dataset with "false" marks. FIG. 2 is a flow diagram that illustrates a workflow for physician review and analysis of medical images according to an exemplary embodiment of the invention, in which a CAD-assisted review of marked images is implementing using a CAD tool according to the invention that generates "false" marks in medical images.

In accordance with exemplary embodiments of the invention, a practitioner (physician, clinician, radiologist, etc.) who is reviewing a "marked" image (which is generated by a CAD tool according to the invention) is aware that one or more false marks may or may not be included in the marked image to purposefully mislead the reviewer. Therefore, the reviewing practitioner cannot have complete trust or blind reliance in the computer-generated CAD marks, thereby ensuring careful and unbiased review of CAD images.

It is to be understood that the systems and methods described herein in accordance with the present invention may be implemented in various forms of hardware, software, firmware, special purpose processors, or a combination thereof. In one exemplary embodiment of the invention, the systems and methods described herein are implemented in software as an application comprising program instructions that are tangibly embodied on one or more program storage devices (e.g., magnetic floppy disk, RAM, CD Rom, DVD, ROM and flash memory), and executable by any device or machine comprising suitable architecture.

It is to be further understood that because the constituent system modules and method steps depicted in the accompanying Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

Referring now to FIG. 1, an exemplary system (10) for analyzing patient image data generally includes a repository of patient records and files (11) (which includes electronic patient image data), a screen display/viewing system (12), a 2D/3D image rendering and visualization system (13), and an image data processing system (14). As explained below, in accordance with one embodiment of the invention, the image data processing system (14) comprises a CAD module (15) that includes one or more methods for automatically detecting and marking potential abnormal anatomical structures in a subject image dataset, and for adding "false" marks in regions that are not detected as containing abnormal anatomical structures. In another embodiment, the image data processing system (14) may comprise one or more modules or methods for performing other automated diagnostic or evaluation functions (16) of image data.

The patient data records and files (11) include patient image data and/or medical images for one or more subject patients. More specifically, the patient data records and files (11) may include digital image data (18) in the form of raw image data, such as raw CT data (radon data) which is acquired during a CT scan or raw data that is acquired using other imaging modalities. Moreover, the digital image data (18) may comprise one or more 2D slices or three-dimensional volumetric images, which are reconstructed from the raw image data and persistently stored. In addition, the patient data records and files (11) may comprise hard-copy 2D and/or 3D medical images (17) including X-ray films, prints, photographs, etc., of images that are reconstructed from acquired image data. For example, the medical images (17) may include a set of X-ray films including 2D slices of a patient that are reproduced from an image dataset acquired during a CT scan of a region of interest of the patient. It is to be understood that although exemplary embodiments of the invention may be described with reference to CT image data that is acquired using a computed tomography (CT) system, the present invention is applicable to other imaging modalities such as MRI, PET, etc.

The screen display/viewing system (12) may be implemented using any system that is suitable for viewing reproduced medical images (17). For instance, the screen display/viewing system (12) may comprise a lighted screen apparatus that can be used by a physician, clinician, radiologist, etc. to view a plurality of X-rays films that are mounted on the apparatus, which are generated from an acquired image data set of multiple CT slices (17). In another exemplary embodiment of the invention, the screen display/viewing system (12) may be implemented using any system that is suitable for scrolling through a plurality of reconstructed 2D slices, for example.

The image rendering and visualization system (13) may comprise any suitable system/tool/application that can process digital image data (18) of an acquired image dataset (or a portion thereof) to generate and display 2D and/or 3D images on a computer monitor. More specifically, the imaging system (13) may be any application that provides 3D/2D rendering and visualization of image data (18), and which executes on general purpose or specific computer workstation having a monitor. Moreover, the imaging system (13) comprises a GUI (graphical user interface), for example, which enables a user to navigate through a 3D image or a plurality of 2D slices.

The image data processing system (14) comprises methods, functions and modules for processing digital image data (18) to provide computer-aided detection and diagnosis. The image data processing system (14) may comprise an application or tool that executes on a general purpose computer or a computer with specialized hardware. The image data processing system (14) receives and processes digital image data (18), which as noted above, may be in the form of raw image data, 2D-reconstructed data (e.g., axial slices), or 3D-reconstructed data such as volumetric image data or multiplanar reformats, or any combination of such formats. The data processing results of the image data processing system (14) can be output to the image rendering/visualization system (13) for generating 2D and/or 3D renderings of image data in accordance with the processing results of system (14), such as superposition of markers, segmentation of organs or anatomical structures, color or intensity variations, and so forth.

In one exemplary embodiment of the invention, the image data processing system (14) comprises a detection module/method (15) (or CAD module) that processes the image data (18) to detect and mark potential abnormal anatomical features in the image data (18). More specifically, the detection module (15) is capable of identifying, or at least localizing, certain features of interest, such as anatomical anomalies in the input image dataset (18) and adding markers to the image data to indicate such features or regions. The markers may comprise pointers (arrows, cross-hairs, etc,) that point to regions of interest having a potential abnormal structure or that point to a center location of a potential lesion or abnormality. Moreover, the markers may be dotted lines that are formed around the perimeter or edge of a potential lesion or which generally encircle a region of interest that is detected as having a potential abnormal structure.

Furthermore, the detection module (15) comprises one or more methods for adding "false" marks (e.g., incorrect or misleading marks) to the image data. The process of adding "false" marks in the image data (18) ensures an unbiased review of computer-generated marks on displayed images during analysis by a physician. Various methods for including false marks will be discussed in further detail below with reference to FIGS. 2 and 3, for example.

In other embodiments of the invention, the image data processing system (14) may comprise one or more additional modules (16) or methods that provide other image data processing functions such as segmenting data or images or feature extraction and classification. Segmentation is method that identifies features of interest by reference to known or anticipated image characteristics, such as edges, identifiable structures, boundaries, changes or transitions in colors or intensities, changes or transitions in spectrographic information, etc. Classification may be used to specifically identify regions of interest, such as by classification as normal or abnormal anatomies or lesions.

It is to be understood that CAD systems and methods according to the present invention for adding false marks to image data may be implemented as extensions to conventional CAD methods or other automated diagnostic methods for processing image data. Further, it is to be appreciated that the exemplary systems and methods described herein can be readily implemented with 3D medical imaging and CAD systems or applications that are adapted for a wide range of imaging modalities (CT, MRI, etc.) and for diagnosing and evaluating various abnormal anatomical structures or lesions such as colonic polyps, aneurisms, lung nodules, etc. In this regard, although exemplary embodiments may be described herein with reference to particular imaging modalities or particular anatomical features, nothing should be construed as limiting the scope of the invention.

Referring now to FIG. 2, a flow diagram illustrates a workflow for physician review and analysis of patient image data according to an exemplary embodiment of the invention. More specifically, FIG. 2 illustrates a workflow for ensuring unbiased physician review of computer marks that are generated using a CAD tool according to an embodiment of the invention. For purposes of illustration, the exemplary method of FIG. 2 will be described with reference to the system of FIG. 1.

Initially, a physician, clinician, radiologist, etc., will perform a preliminary (CAD-unassisted) review and analysis of patient image data of a subject patient (step 20) to identify potential abnormal anatomical structures or disease states. For example, in one embodiment of the invention, the physician could use the screen display/review system (12) (FIG. 1) to review one or more x-ray films of 2D image slices, which are generated from an image dataset acquired via a CT exam, for example.

In another exemplary embodiment, the physician could review 2D and/or 3D renderings of the image dataset, which are displayed on a computer monitor to identify possible abnormal features. For example, the physician can use the image visualization system (13) (FIG. 1) to render and display 2D and/or 3D images from the input image dataset, and navigate through the displayed images using a suitable GUI to identify potential abnormal features. In such case, the visualization system (13) simply constructs and displays 2D and/or 3D images for review by the physician, but does not perform CAD related functions to assist in the analysis, nor display images that are rendered and displayed based on CAD results.

The physician will generate a preliminary report of his/her initial findings based on the CAD-unassisted review of the patient image data (step 21). This report may comprise preliminary diagnostic decisions and findings of the physician, including references to particular regions (or features) of interest, which are believed by the physician to include (or to be) potential lesions or anatomical anomalies.

Thereafter, the physician will perform a CAD-assisted review of the patient image data to verify or reconcile his/her preliminary findings. More specifically, in one exemplary embodiment of the invention, a CAD-assisted review commences by processing the image dataset (which was the subject of the preliminary review) using a CAD tool according to the invention that is capable of detecting and marking potential lesions or other abnormal anatomical structures in the image data, and possibly adding one or more false marks in the image dataset (step 22). More specifically, by way of example with reference to FIG. 1, a CT image dataset (18) can be input to the CAD module (15) to detect potential abnormal anatomical features in the image data (18) and generate marks that are placed around or adjacent the detected potential abnormalities in the image data. Furthermore, depending on the methods implemented in the detection module (15), one or more false marks may (or may not) be added to the image data. Various methods for adding false marks to image data according to the invention will be discussed in further detail below.

The physician will then perform a CAD-assisted review of the patient image data based on 2D and/or 3D renderings of the "marked" image data that are displayed on a display device (step 23). For example, the output of the CAD module (15) ("marked" image data) can be input to the image rendering/visualization system (13), which generates and displays one or more 2D and/or 3D medical images showing the computer-generated marks, which may be true and/or false markings, based on the results of the detection process. In other words, the displayed images are marked or otherwise annotated with a localized identification of potential abnormalities that are detected by the CAD module (15), and may further have one or more false marks or annotations.

Advantageously, in accordance with the present invention, the potential addition by the CAD module (15) of one or more false marks or annotations ensures an unbiased review of the computer-generated marks in the displayed images during the physician's CAD-assisted analysis. In particular, assuming that the physician is aware that the CAD tool (15) can possibly add one or more false marks in the medical images, the physician cannot have complete trust in the CAD marks and will be compelled to perform a more detailed and careful analysis of the computer-generated marks. In other words, the potential addition of one or more false marks ensures that the physician will perform an independent CAD-unassisted review, and/or a detailed CAD-assisted review, rather than "blindly" relying on the "marked output" of the CAD tool.

Following the CAD-assisted review, the physician can augment his/her preliminary report based final diagnostic decision (step 24). This final diagnostic report may or may not be the same as the preliminary report, depending on whether the physician determines additional diagnostic information provided by the CAD tool to be significant. Following the final diagnostic report, the physician can recommend a course of further action, which can include no further action or further follow-up examinations or procedures.

Figure 3:
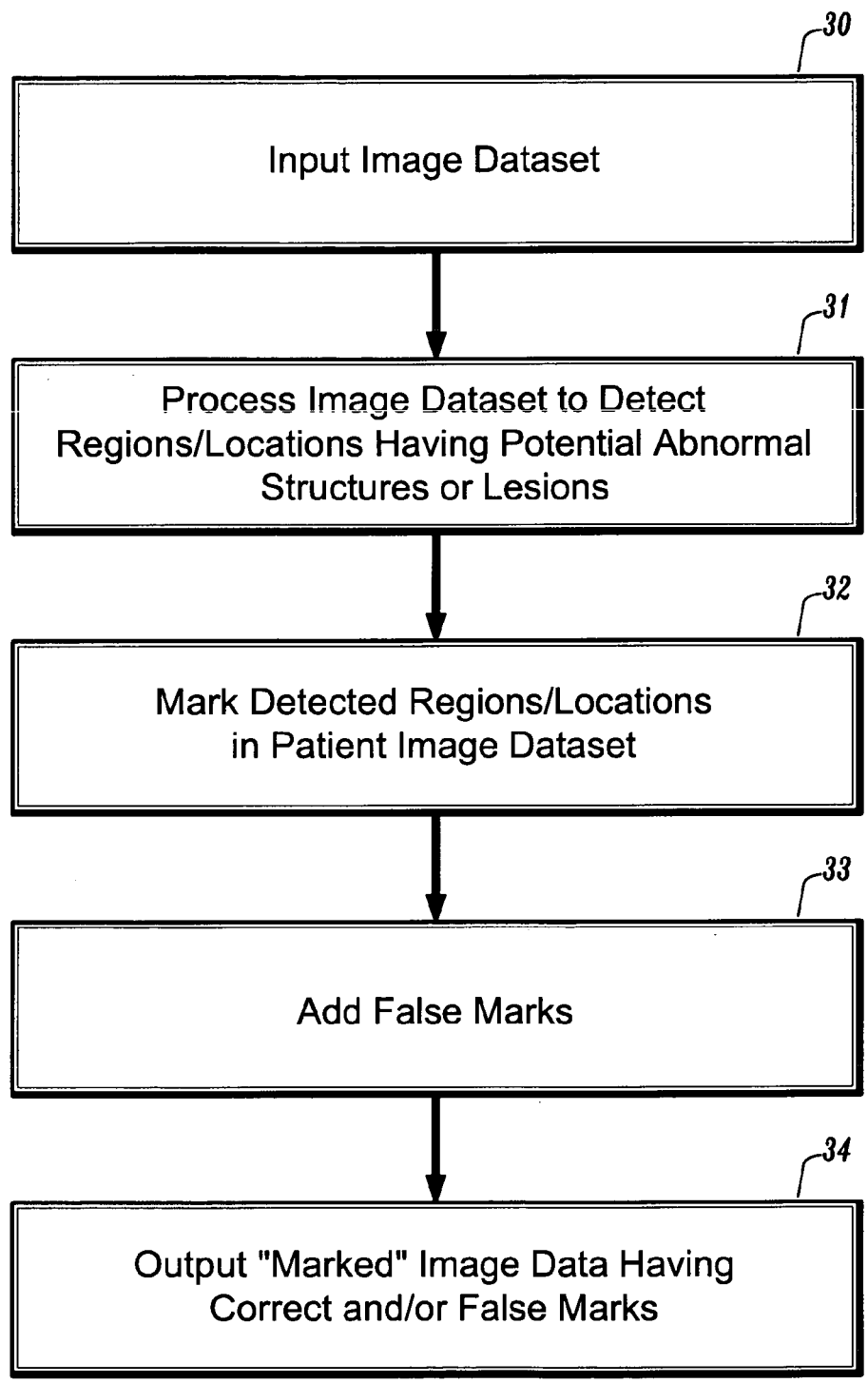
FIG. 3 is a flow diagram of a CAD method according to an exemplary embodiment of the invention.

FIG. 3 is a flow diagram that illustrates a CAD method according to an exemplary embodiment of the invention. In one embodiment of the invention, FIG. 3 depicts a method for implementing step 22 of FIG. 2. In another embodiment of the invention, FIG. 3 illustrates a mode of operation of a CAD module (15) of FIG. 1. Referring to FIG. 3, an image dataset of a subject patient is input to a CAD tool (step 30). The input image dataset is processed to detect and identify regions (or features) of interest in the image dataset having potential abnormal anatomical structures (step 31). It is to be understood that the detection process (step 31) may be implemented using any detection method which is suitable for the imaging modality (e.g., CT) of the input image data and which is specifically or generally adapted for detecting anatomical abnormalities (e.g., cancer, polyps, nodules, etc.) that are the subject of diagnosis. The detection process will mark those regions of interest in the input image dataset, which are determined to be potential lesions or other abnormal structures (step 32). Furthermore, in accordance with the present invention, the detection process may add one or more false marks in the image dataset (step 33). Thereafter, the "marked" image dataset is output from the CAD detection module (step 34) and further processed for rendering and displaying 2D and/or 3D images showing the computer-generated correct and/or false marks.

It is to be appreciated that various methods according to exemplary embodiments of the invention can be employed for implementing the false marking process (step 33). AS noted above, in accordance with the exemplary embodiments described herein, it is assumed that the individual performing a CAD-assisted review of "marked" images generated by a CAD tool is aware that one or more false marks (or annotations) may be included in displayed images or more generally that one or more marks may be included to purposely mislead the reviewer.

In one embodiment of the invention, a detection process will add either a fixed or random number of false marks to the image dataset. More specifically, in one embodiment of the invention, the detection process may be programmed to add a fixed number of false marks in the image data. The false marks may be randomly inserted in random regions that are determined to not have abnormal structures or lesions, or the detection process can be programmed to falsely mark anatomical structures that resemble lesions or anomalies of interest, which are being investigated. For instance, when diagnosing for cancer, false marks may be added to regions that include scar tissues, which may have features similar to cancer.

In another embodiment of the invention, rather than always adding a fixed number of false marks, a CAD method will add a random number of marks for each invocation of the detection process. For instance, a random number of false marks may include the addition of zero (0) marks or 1 or more false marks. If the physician knows that a fixed number of false marks are always added to the image data, the physician may let down his guard after finding a fixed number of obviously incorrect marks, whereas the addition of a random number of marks each time the CAD tool is used would prevent such circumstance. Again, the random marks may be added to random locations, or may be added at regions having structures that are similar to the abnormal structures being investigated.

In yet another embodiment of the invention, the detection process may be configured to randomly perturb the location of a computer-generated mark, to ensure that the physician analyzes areas surrounding the marked region or structure. The maximum extent of the perturbation could be limited. More specifically, the detection process may shift a mark from a location where a potential lesion or abnormality is believed to be located, thus ensuring that the physician carefully reviews the area surrounding the mark. By way of example, assuming a physician is reviewing image data of a colon for the purpose of finding potential polyps. If a computer mark was inserted in a location of the colon lumen, the physician would not be able to assume that the mark was false. Instead, the physician would be compelled to search the surrounding area (colon wall tissue) to identify a potential polyp.

In another embodiment of the invention, a CAD detection tool according to the invention can be adapted to not only add false marks, but also not include one or more marks at locations in the image data which the detection method determines to actually have potential lesions or abnormalities. In this manner, if the physician is aware that a computer generated image does not include all potential marks detected by the CAD detection system, the physician will not be able to blindly trust the output and be compelled to carefully review marked image.

It is to be appreciated that systems and methods according to the invention, which provide automated CAD methods for ensuring physician review of computer-generated marks, can be effectively implemented for enhancing the value and quality of clinical data and patient records. Systems and methods according to the invention ensure higher quality patient data that can be used in automated systems that provide standardized assessment of care outcomes and processes, regulatory oversight of healthcare providers, medical billing and accurate calculation of fees or reimbursements, etc.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for automatic detection of medical conditions in medical images, comprising the steps of:
    inputting image data of a patient to a computer-aided detection (CAD) tool;
    processing the image data to detect regions of interest in the image data that have potential medical conditions, wherein during the detection process, the CAD tool:
        marks a region of interest in the image data that is determined to have a potential medical condition; and
        adds a false mark to the image data; and
    outputting, from the CAD tool, marked image data that includes one or more marks that identify regions of interest determined to have potential medical conditions and one or more false marks,
    wherein the one or more false marks are included in the marked image data so that a medical practitioner is compelled to manually review each mark in the marked image data rather than rely solely on results of the CAD tool's detection process.

2. The method of claim 1, wherein the step of adding a false mark comprises adding a fixed number of false marks in the image data.

3. The method of claim 2, wherein the fixed number of false marks are added to random locations in the image data.

4. The method of claim 1, wherein the step of adding a false mark comprises adding a random number of false marks in the image data for each invocation of the automatic detection method.

5. The method of claim 1, wherein the step of adding a false mark comprises marking a region or structure in the image data that has features similar to a medical condition being evaluated.

6. The method of claim 1 wherein the step of adding a false mark comprises randomly perturbing a location at which a mark that identifies a region of interest determined to have a potential medical condition is inserted in the image data.

7. The method of claim 1, wherein the medical condition comprises an abnormal anatomical structure.

8. The method of claim 1, wherein the medical condition comprises a lesion.

9. The method of claim 1, further comprising rendering the marked image data to display one or more 2D, 3D, or both 2D and 3D images having the one or more marks that identify regions of interest determined to have potential medical conditions and the one or more false marks.

10. The method of claim 1, further comprising the step of not including a mark in the image data at a region of interest determined to have a potential medical condition.

11. A computer readable medium tangibly embodying a program of instructions executable by a processor to perform method steps for automatic detection of medical conditions in medical images the method step comprising:
    receiving image data of a patient;
    performing a computer-aided detection (CAD) process to detect regions of interest in the image data that have potential medical conditions, wherein the CAD process:
        marks a region of interest in the image data that is determined to have a potential medical condition; and
        adds a false mark to the image data; and
    outputting marked image data that includes one or more marks that identify regions of interest determined to have potential medical conditions and one or more false marks,
    wherein the one or more false marks are included in the marked image data so that a medical practitioner is compelled to manually review each mark in the marked image data rather than rely solely on results of the CAD process.

12. The computer readable medium of claim 11, wherein the instructions for adding a false mark comprise instructions for adding a fixed number of false marks in the image data.

13. The computer readable medium of claim 12, wherein the fixed number of false marks are added to random locations in the image data.

14. The computer readable medium of claim 11, wherein the instructions for adding a false mark comprise instructions for adding a random number of false marks in the image data for each invocation of the automatic detection method.

15. The computer readable medium of claim 11, wherein the instructions for adding a false mark comprise instructions for marking a region or structure in the image data that has features similar to a medical condition being evaluated.

16. The computer readable medium of claim 11, wherein the instructions for adding a false mark comprise instructions for randomly perturbing a location at which a mark that identifies a region of interest determined to have a potential medical condition is inserted in the image data.

17. The computer readable medium of claim 11, wherein the medical condition comprises an abnormal anatomical structure.

18. The computer readable medium of claim 11, wherein the medical condition comprises a lesion.

19. The computer readable medium of claim 11, further comprising instructions for rendering the marked image data to display one or more 2D, 3D, or both 2D and 3D images having the one or more marks that identify regions of interest determined to have potential medical conditions and the one or more false marks.

20. The computer readable medium of claim 11, further comprising instructions for not including a mark in the image data at a region of interest determined to have a potential medical condition.

* * * * *